US007939580B2

(12) United States Patent
Eckert et al.

(10) Patent No.: US 7,939,580 B2
(45) Date of Patent: May 10, 2011

(54) DENTAL COMPOSITION CONTAINING EPOXY FUNCTIONAL POLYMERIZABLE COMPOUNDS

(75) Inventors: Adrian S. Eckert, Munich (DE); Peter Bissinger, Diessen (DE); Karsten Dede, Landsberg (DE); Thomas Klettke, Diessen (DE); Christoph Thalacker, Weilheim (DE); Dwight W. Jacobs, Hudson, WI (US); Roger A. Mader, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 751 days.

(21) Appl. No.: 11/572,051

(22) PCT Filed: Jul. 14, 2004

(86) PCT No.: PCT/EP2004/007748
§ 371 (c)(1),
(2), (4) Date: Jan. 12, 2007

(87) PCT Pub. No.: WO2006/005365
PCT Pub. Date: Jan. 19, 2006

(65) Prior Publication Data
US 2008/0319102 A1    Dec. 25, 2008

(51) Int. Cl.
*A61K 6/08* (2006.01)
*A61C 5/04* (2006.01)
(52) U.S. Cl. .................. 523/116; 433/226; 522/908
(58) Field of Classification Search .................. 523/113, 523/115, 116
See application file for complete search history.

(56) References Cited

U.S. PATENT DOCUMENTS

| | | | |
|---|---|---|---|
| 3,715,334 A | 2/1973 | Karstedt | |
| 3,775,352 A | 11/1973 | Leonard | |
| 3,814,730 A | 6/1974 | Karstedt | |
| 3,933,880 A | 1/1976 | Bergstrom et al. | |
| 3,971,754 A | 7/1976 | Jurecic | |
| 4,391,590 A | 7/1983 | Dougherty | |
| 4,449,938 A * | 5/1984 | Pollak | 523/116 |
| 4,705,836 A | 11/1987 | Ohtsuka et al. | |
| 4,767,798 A | 8/1988 | Gasser et al. | |
| 4,788,268 A | 11/1988 | Lau et al. | |
| 5,145,886 A | 9/1992 | Oxman et al. | |
| 5,165,890 A | 11/1992 | Discko | |
| 5,233,006 A | 8/1993 | Wolter et al. | |
| 5,322,440 A | 6/1994 | Steele | |
| 5,750,589 A | 5/1998 | Zech et al. | |
| 6,046,250 A | 4/2000 | Boardman et al. | |
| 6,084,004 A * | 7/2000 | Weinmann et al. | 522/25 |
| 6,376,569 B1 | 4/2002 | Oxman et al. | |
| 6,387,981 B1 | 5/2002 | Zhang et al. | |
| 6,566,413 B1 | 5/2003 | Weinmann et al. | |
| 6,572,693 B1 | 6/2003 | Wu et al. | |
| 6,624,236 B1 | 9/2003 | Bissinger et al. | |
| 6,653,375 B2 | 11/2003 | Moszner et al. | |
| 2002/0040103 A1 | 4/2002 | Schmid | |
| 2004/0162364 A1* | 8/2004 | Su et al. | 523/115 |
| 2004/0242723 A1* | 12/2004 | Jin et al. | 523/115 |
| 2005/0252413 A1 | 11/2005 | Kangas et al. | |
| 2005/0252414 A1 | 11/2005 | Craig et al. | |
| 2005/0256223 A1 | 11/2005 | Kolb et al. | |

FOREIGN PATENT DOCUMENTS

| | | | |
|---|---|---|---|
| EP | 0238025 A1 * | 9/1987 | |
| EP | 0451709 A2 * | 10/1991 | |
| EP | 0480238 A * | 4/1992 | |
| EP | 0897710 A1 * | 2/1999 | |
| WO | WO 98/22521 * | 5/1998 | |
| WO | WO 98/33645 * | 8/1998 | |
| WO | WO 98/47046 * | 11/1998 | |
| WO | WO 98/47047 * | 11/1998 | |
| WO | WO 99/62894 * | 12/1999 | |
| WO | WO 00/19967 * | 4/2000 | |
| WO | WO 01/30305 * | 5/2001 | |
| WO | WO 01/30306 * | 5/2001 | |
| WO | WO 01/30307 * | 5/2001 | |
| WO | WO 01/92271 A1 * | 12/2001 | |
| WO | WO 01/95862 A1 * | 12/2001 | |
| WO | WO 02/066535 * | 8/2002 | |
| WO | WO 03/063804 * | 8/2003 | |
| WO | WO 2006/005364 * | 1/2006 | |
| WO | WO 2006/005365 A1 * | 1/2006 | |

OTHER PUBLICATIONS

Houben-Weyl, Methoden d. Organischen Chemie, vol. VI/3, p. 385-405., Georg Thieme Verlag, Stuttgart, 1965, 4. edition.*
Houben-Weyl, Methoden d. Organischen Chemie, vol. VI/3, p. 57 (first preparation example) resp. p. 56 (first prep. Example), Georg Thieme Verlag, Stuttgart, 1965, 4. edition.*
OECD Guideline 471 and ISO 10993-3 (2003).*
Tarbell et al., The Rearrangement of 4-Crotyloxy-3,5-Dichlorobenzoic Acid, *J. Am. Chem. Soc.*, 1942, 64(5), 1066-1070.
Marciniec, B., Comprehensive Handbook on Hydrosilylation, p. 8-98., Pergamon Press, Oxford, 1992.
Houben-Weyl, Methoden d. Organ. Chemie, vol. VI/3, p. 49ff., Georg Thieme Verlag, Stuttgart, 1965, 4. edition.
EN ISO 4049.
DIN EN 9917-1.
DIN EN 9917-2. International Preliminary Report on Patentability and Written Opinion for PCT/EP2004/007748; 6 pgs.

* cited by examiner

*Primary Examiner* — Mark Eashoo
*Assistant Examiner* — David Karst

(57) ABSTRACT

The present invention relates to dental compositions comprising a halogenated epoxy functional ether derivative comprising at least one aryl alkyl ether moiety, at least one halogen atom attached to each aryl residue of the aryl alkyl ether moieties, at least two aliphatic epoxy moieties, no glycidyl ether structure, an initiator, optionally filler and optionally additive components selected from the group of modifiers, dyes, pigments, thixotropic agents, flow improvers, polymeric thickeners, surfactants, odorous substances, diluting agent(s) and flavorings.

18 Claims, No Drawings

DENTAL COMPOSITION CONTAINING EPOXY FUNCTIONAL POLYMERIZABLE COMPOUNDS

The present invention relates to a curable dental composition containing epoxy functional polymerizable compounds. The composition has improved properties and can be used e.g. as a dental filling material.

BACKGROUND

Composites are well known dental restorative materials on the market. However, most of the organic based dental restoratives to date are based on methacrylate and/or acrylate chemistries. They usually cure via a light induced radical polymerization of unsaturated components. They often exhibit a very high stress upon curing due to the high polymerization shrinkage. It is thought that dental restorative materials based on oxirane chemistries may exhibit lower shrinkage and lower polymerization stress.

WO 98/47046 describes a photocurable, addition polymerizable composition which contains an epoxy resin and a photoinitiator system. The epoxy resin includes glycidyl ether monomers.

WO 00/19967 discloses a dental composition useful for making dental protheses or dental restoration comprising epoxy reactive functions which are polymerizable via a cationic cure process. The epoxy reactive functions include cycloaliphatic epoxides, glycidyl ether or oxetanes.

WO 98/22521 describes polymerizable substances containing an epoxide or a mixture of epoxides, a filler material, initiators, inhibitors and/or accelerators. The substances include cycloaliphatic epoxy functions with a relatively high viscosity.

WO 98/33645 describes a die adhesive or encapsulant of epoxy siloxane and polyepoxy resin. The polymerizable mixture contains a cycloaliphatic, epoxy-functional siloxane and a non-silicon-containing di-, tri- or polyepoxy resin. This resin, among others, may be a resin of diglycidyl ether of brominated bisphenol A.

WO 02/066535 discloses polymerizable preparations based on silicon compounds comprising aliphatic and cycloaliphatic epoxide groups. The preparations disclosed therein contain polymerizable compounds with at least one cycloaliphatic epoxide group per molecule.

A disadvantage of the dental composites known from the state of the art is that the polymerizable compounds based on glycidyl ethers are not very reactive in the polymerization reaction. A further drawback is, that some of the components of the dental composite materials form color during curing which is not desired for esthetic reasons. The formation of color can be measured on the cured composition using values on the L* a* b* scale. The a* and b* values, which represent the amount of red and yellow coloration, respectively, are particularly important values to indicate the esthetic properties of the cured dental compositions. The common dyes for dental compositions which can be added to the composition to correct the color if needed are yellow and red dyes. Thus, low a* and b* values are desired.

It is thus an object of the present invention to alleviate one or more of the problems mentioned above.

It is another object of the present invention to provide a composition with improved properties, especially higher reactivities of the epoxy moieties in cure reactions together with low color formation during curing.

SUMMARY OF THE INVENTION

The terms "comprise" and "contain", within the meaning of the invention, include a non-exhaustive list of features. Likewise, the word "one" or "a" is to be understood in the sense of "at least one".

The term "dental composition" according to the invention is a curable composition to be used in the dental field for various purposes, for example, such as adhesives, restoratives and cements. Typically, such materials are used in dental applications in small amounts like a few grams.

It has been found that one or more of the above mentioned objects can be achieved by providing a composition as described in the text below.

Surprisingly, it has been found that using halogenated epoxy functional ether derivatives comprising polymerizable groups such as aliphatic epoxies that do not contain glycidyl ether moieties provide curable dental compositions with improved properties.

Thus, the present invention relates to a curable dental composition comprising
a) at least one halogenated epoxy functional ether derivative each comprising:
   at least one aryl alkyl ether moiety wherein each aryl residue is substituted with at least one halogen atom; and
   at least one aliphatic epoxy moiety;
   wherein said derivative has no glycidyl ether moieties; and
b) initiator,
c) optionally filler,
d) optionally additive components selected from the group of modifiers, stabilizers, dyes, pigments, thixotropic agents, flow improvers, polymeric thickeners, surfactants, odorous substances, diluting agent(s) and flavorings.

One or more halogenated epoxy functional ether derivatives can be used alone or in a mixture with other components comprising aliphatic epoxy and/or cycloaliphatic epoxy functionalities and/or polymerizable compounds of other functionalities than epoxy as reactive components to provide dental compositions within the scope of the invention. Compositions of the invention may also contain other reactive and/or unreactive components if desired.

The present invention also relates to a method of producing the dental composition as described below.

Additionally, the present invention relates to a method of using the composition as described below.

It was found that the formation of color during curing (e.g. light induced cationic ring opening polymerization) is significantly reduced by using the halogenated epoxy functional ether derivative in the curable dental composition of the invention.

The reactivity of the halogenated epoxy functional ether derivative is generally higher than that of similar aliphatic epoxy functional aryl alkyl ether derivatives that are known from the literature.

Surprisingly, the halogenated epoxy functional ether derivative preferably has a comparably high refractive index and high molecular mass. The refractive index of halogenated epoxy functional ether derivative may be high especially in comparison to similar aliphatic epoxy functional aryl alkyl ether derivatives known from the state of the art. This is of some importance for dental materials because they must resist staining and/or swelling by uptake of water and/or uptake of water-soluble dyes (e.g. from coffee, tea, red wine).

With the halogenated epoxy functional ether derivate of the invention a dental material with improved esthetic properties can be achieved.

Another advantage of the dental compositions described by the invention is their appropriate lipophilicity.

Preferably, the halogenated epoxy functional ether derivatives have a refractive index from 1.530 to 1.680, preferably from 1.560 to 1.650, more preferably from 1.590 to 1.620.

Preferably, the halogenated epoxy functional ether derivatives have an average molecular mass from 400 to 10 000 g/mol, preferably from 600 to 5000 g/mol, more preferably from 800 to 2000 g/mol.

Preferably, the halogenated epoxy functional ether derivatives have a viscosity below 40 Pas, preferably below 20 Pas and more preferably below 5 Pas.

Preferably, the dental composition of the invention can comprise from 1 wt.-% to 90 wt.-%, preferably from 3 wt.-% to 65 wt.-% and more preferably from 10 wt.-% to 30 wt.-% of one more halogenated epoxy functional ether derivatives.

Preferably, the amount of initiator can range from 0.01 to 25 wt.-%, preferably from 0.5 to 10 wt.-%, more preferably from 1 to 3 wt.-%.

If a filler is present in the dental composition it is preferably present in an amount from 3 to 90 wt.-%, preferably from 25 to 80 wt.-% and more preferably from 50 to 75 wt.-%.

One or more of the optional additive components can be present in an amount from 0 to 25 wt.-%, preferably from 0 to 15 wt.-%, more preferably from 0 to 3 wt.-%.

All of these above mentioned ranges are calculated as wt.-% of the curable composition.

Preferably, the curable dental composition of the invention possess at least one of the following characteristics when in the cured state:

The opacity of the cured dental composition preferably is from 10% to 88%. It should more preferably be from 40% to 86% and most preferably from 70% to 84%.

The compressive strength of the cured dental composition is preferably greater than about 150 MPa, preferably greater than about 200 MPa, and more preferably greater than about 250 MPa.

The flexural strength of the cured dental composition is preferably greater than about 50 MPa, preferably greater than about 65 MPa, and more preferably greater than about 80 MPa.

The color formation (a* value) of the cured dental composition should be from −15 to 0, preferably from −8 to 0, more preferably from −8 to −4.

The color formation (b* value) of the cured dental composition should be from 0 to 18, preferably from 1 to 16, more preferably from 2 to 14. Preferably it should not exceed 14.

The mutagenicity of halogenated epoxy functional ether derivatives as determined by the AMES mutagenicity testing protocol should preferably be negative.

The halogenated epoxy functional ether derivative comprises the following chemical moieties:
- at least one, preferably two, and more preferably two to four aryl alkyl ether moieties wherein said aryl groups are preferably substituted with at least one, and more preferably two halogen atoms,
- at least two, preferably three to four, more preferably three aliphatic epoxy moieties,
- no glycidyl ether structures.

In one embodiment of the invention, the dental composition comprises one or a mixture of different halogenated epoxy functional ether derivatives each of which comprise at least one group of the following general formula (A'):

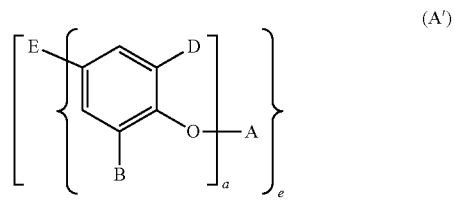

wherein
each A independently represents an alkyl, cycloalkyl, aryl alkyl or aryl cycloalkyl group having one to 30 carbon atoms, or an aliphatic epoxy moiety having 4 to 30 carbon atoms, wherein one or more C or H atoms can be replaced by Br, Cl, N or O,
each B independently represents H, Br, Cl or (2,3-epoxy)-propyl and preferably is Cl;
each D independently represents Br or Cl and preferably is Cl;
each E independently represents H, an alkyl, cycloalkyl, aryl alkyl or aryl cycloalkyl group having one to 100 carbon atoms, wherein one or more C or H atoms can be replaced by Br, Cl, N or O;
a is 1, 2, 3 or 4 (preferably 3, more preferably 1 or 2)
e is 1, 2, 3 or 4 (preferably 3 or 2);
wherein at least one of a or e= 1 and
the aliphatic epoxy moiety of substituent A does not contain a glycidyl ether structure and does not form a glycidyl ether with the adjacent O-atom.

Preferred embodiments the halogenated epoxy functional ether derivative can be characterized by the formulas (I-III) depending on the molecular structure of the halogenated epoxy functional ether derivative as well as on the numbers a or e of the aryl alkyl ether moieties of general formula (A').

In a preferred embodiment the halogenated epoxy functional ether derivative comprises only one aryl alkyl ether moiety and an epoxy alkyl residue as A (i.e., a=1, e=1 and A=epoxy alkyl) and can be characterized by formula (I):

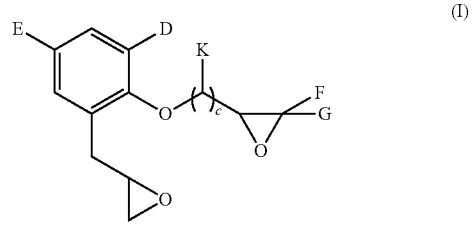

wherein
D represents Br or Cl, and preferably is Cl,
E represents H, Br or Cl, preferably Cl,
F represents H, an alkyl or aryl group having one to 6 carbon atoms, wherein one or more C or H atoms can be replaced by Br, Cl, N or O;
G represents H, an alkyl or aryl group having one to 6 carbon atoms, wherein one or more C or H atoms can be replaced by Br, Cl, N or O;
each K independently represents H, methyl or ethyl;
c is 2 to 11, preferably 5, more preferably 4, most preferably 2 or 3;
and wherein the other indices are as defined above.

The following compounds are preferred examples according to formula (I) of the halogenated epoxy functional ether derivative:

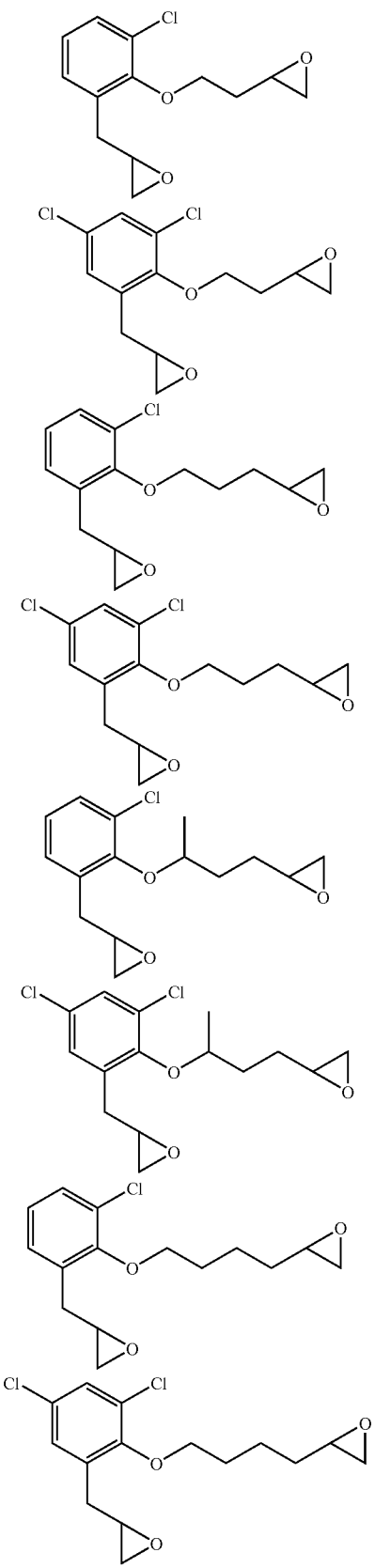

one aryl alkyl ether moiety and B is a (2,3-epoxy)-propyl residue (i.e. a ≧2 and e=1 and B=(2,3-epoxy)-propyl) and can be characterized by formula (II):

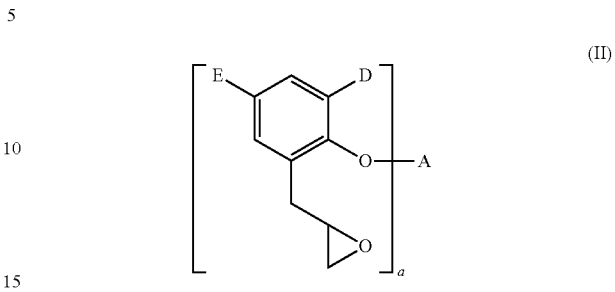

wherein

A represents an alkyl, cycloalkyl, aryl alkyl or aryl cycloalkyl group having one to 12 carbon atoms, wherein one or more C or H atoms can be replaced by Br, Cl, N or O;

each D independently represents Br or Cl, and preferably is Cl;

each E independently represents H, Br or Cl, and preferably is Cl;

a is 2, 3 or 4, preferably is 3, and more preferably is 2;

and wherein the other indices are as defined above.

The following compounds are examples of preferred halogenated epoxy functional ether derivatives according to formula (II):

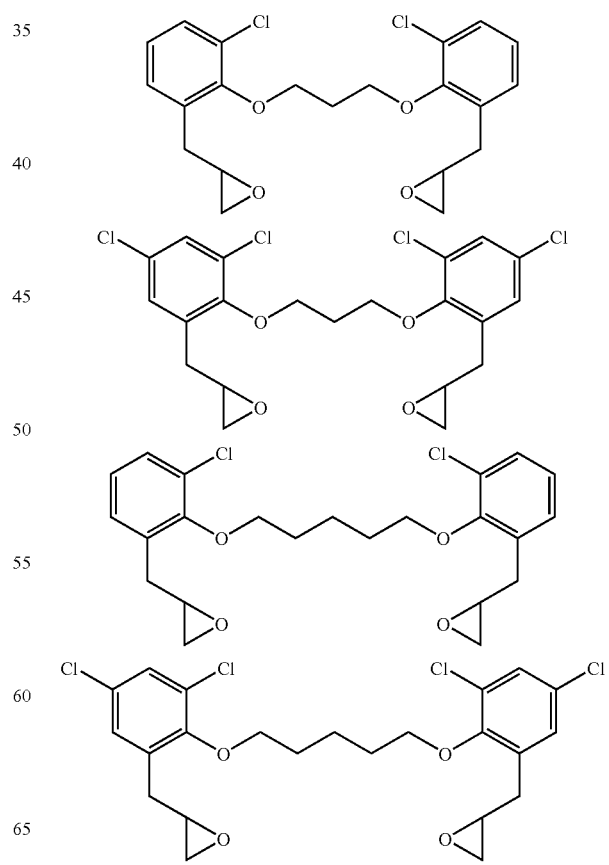

In a preferred embodiment of the invention, the halogenated epoxy functional ether derivative comprises more than

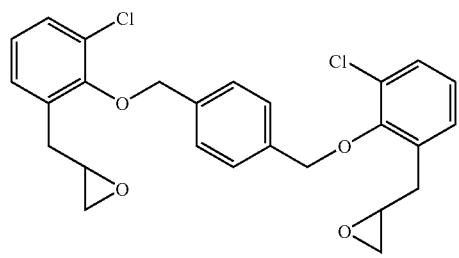
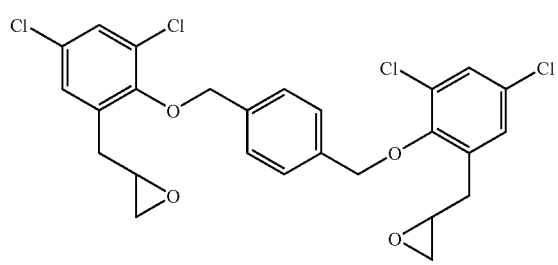
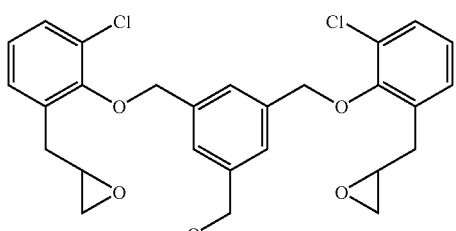
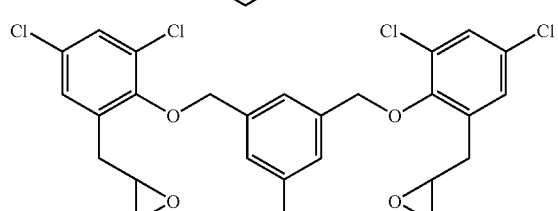
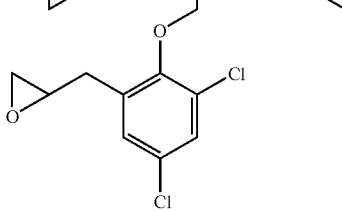
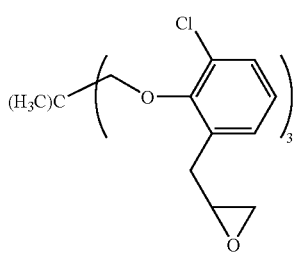

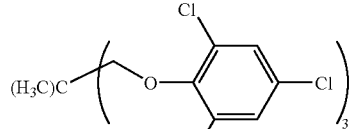
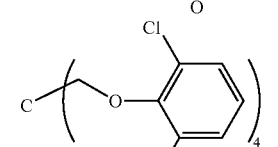
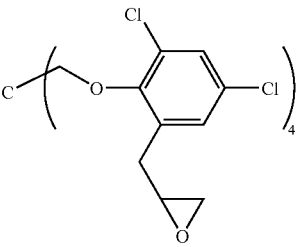

In another preferred embodiment, the halogenated epoxy functional ether derivative comprises more than one aryl alkyl ether moiety and epoxy alkyl residues as A (i.e. a=1 and e≧2 and A=epoxy alkyl with one to 12 carbon atoms) and can be characterized by formula (III):

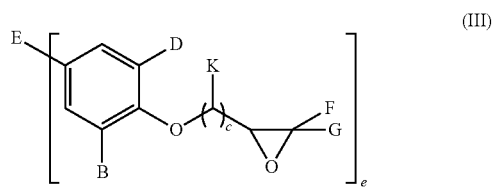

wherein
each B independently represents H, Br or Cl, and preferably is Cl;
each D independently represents Br or Cl, and preferably is Cl;
E represents an alkyl, cycloalkyl, aryl alkyl or aryl cycloalkyl group having one to 80 carbon atoms, wherein one or more C or H atoms can be replaced by Br, Cl, N or O;
each F independently represents H, an alkyl or aryl moiety having one to 6 carbon atoms and wherein one or more C or H atoms can be replaced by Br, Cl, N or O;
each G independently represents H, an alkyl or aryl moiety having one to 6 carbon atoms and wherein one or more C or H atoms can be replaced by Br, Cl, N or O;
each K independently represents H, methyl or ethyl,
c=2-11, preferably 4, more preferably 2 or 3,
e is 2, 3 or 4, preferably is 3, and more preferably is 2;
and wherein the other indices are as defined above.
The following compounds are preferred examples of halogenated epoxy functional ether derivatives according to formula (III):

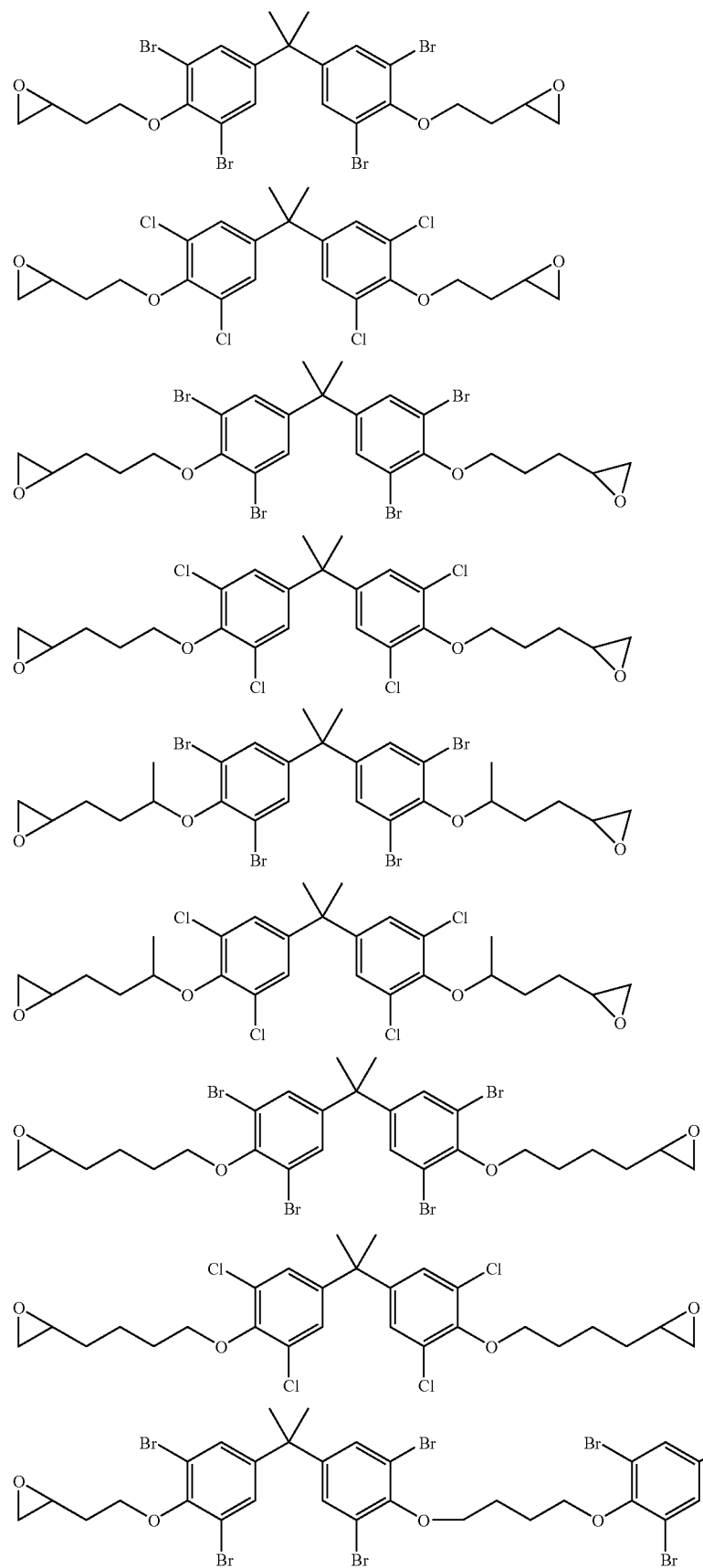

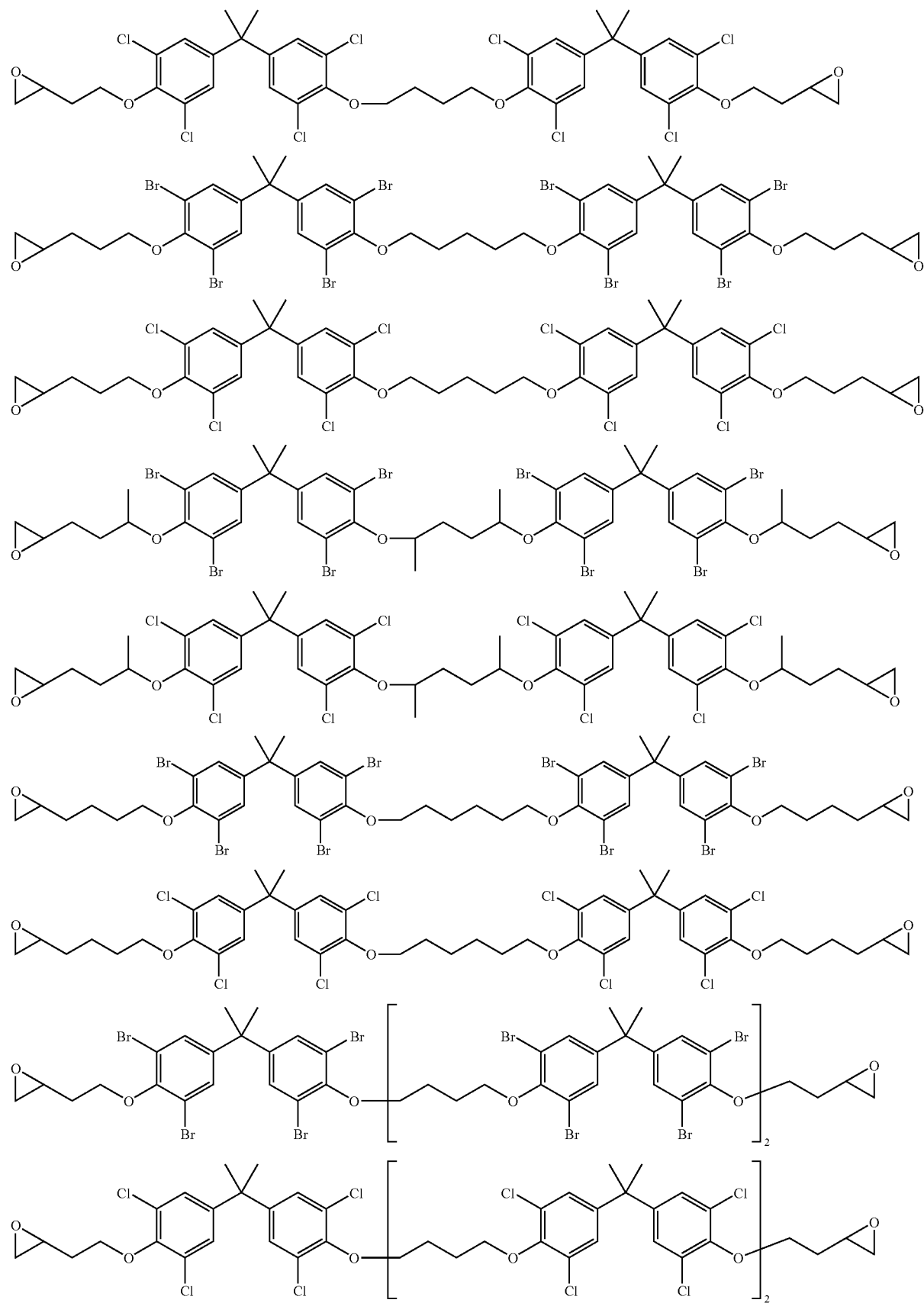

-continued

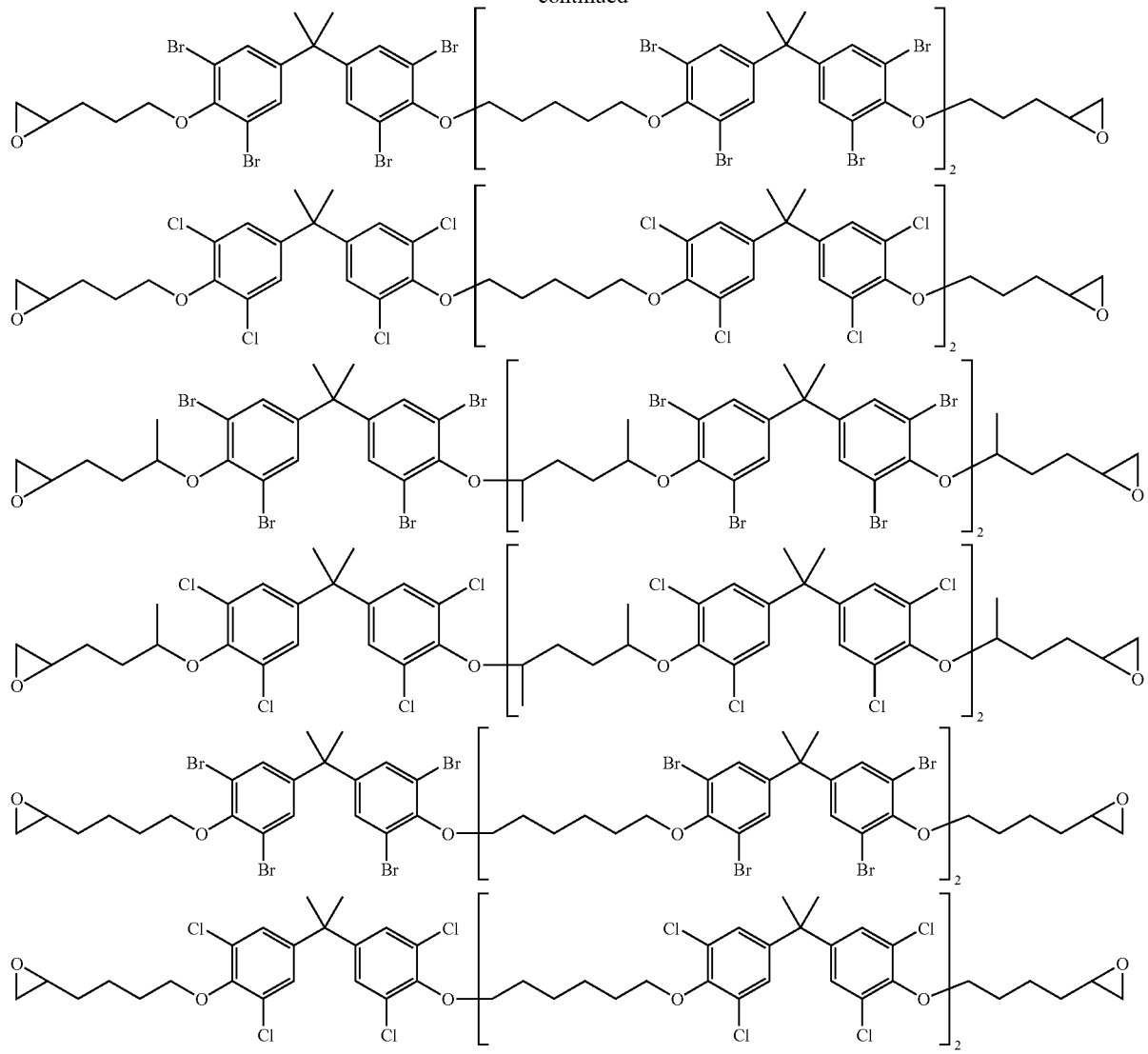

Useful initiators can initiate curing of the halogenated epoxy functional ether derivative of the curable composition.

Such initiators can be cure via light cure or chemical cure or redox cure reactions. All types of initiators are well known to the skilled person in the art.

Examples of such initiators include Lewis or Bronsted acids, or compounds which liberate such acids and which initiate the polymerization, for example $BF_3$ or ether adducts thereof (e.g., $BF_3.THF$, $BF_3*Et_2O$), $AlCl_3$, $FeCl_3$, $HPF_6$, $HAsF_6$, $HSbF_6$ or $HBF_4$ or substances which initiate the polymerization after irradiation by UV or visible light or by means of heat and/or pressure, such as e.g. (eta-6-cumene)(eta-5-cyclopentadienyl)iron hexafluorophosphate, (eta-6-cumene)(eta-5-cyclopentadienyl)iron tetrafluoroborate, (eta-6-cumene)(eta-5-cyclopentadienyl)iron hexafluoroantimonate, substituted diaryliodonium salts and triarylsulphonium salts. Accelerators can be employed in combination with the initiators. Examples of useful accelerators include peroxy compounds of the perester, diacyl peroxide, peroxydicarbonate and hydroperoxide type. Hydroperoxides are preferably used. Cumene hydroperoxide in an approximately 70 to 90% solution in cumene is a particularly preferred accelerator. The ratio of photoinitiator to cumene hydroperoxide can be varied within wide limits, e.g., from 1:0.001 to 1:10, but the ratio preferably used is 1:0.1 to 1:6, and most preferably 1:0.5 to 1:4. The use of complexing agents, such as oxalic acid, 8-hydroxyquinoline, ethylenediaminetetraacetic acid and aromatic polyhydroxy compounds is also possible.

Likewise, initiator systems consisting of different components can be used in the invention, for example, described in EP 0 897 710 A1, WO 98/47046, or WO 98/47047. Preferred initiator systems include 1,2-diketones (as e.g. Campherquinone), iodoniumium salts with poor coordinating anions (as e.g. Tolylcumyliodonium tetrakis(pentafluorophenyl)borate or Tolylcumyliodonium tetrakis(3,5-bis(trifluoromethyl)-phenyl)borate) together with tertiary aromatic amines (as e.g. benzoates like 2-butoxyethyl 4-(dimethylamino)benzoate, ethyl 4-(dimethylamino)benzoate) and/or suitable polycondensed aromatic compounds (as e.g. anthracene).

The composition of the present invention may also include one or more fillers. Preferably used are inorganic fillers like quartz, ground glasses, silica gels as well as pyrogenic silicic acids or precipitation silicic acids or their granules. X-ray-opaque fillers are also preferably used, at least partially. These can be, for example, X-ray-opaque glasses, such as glasses which contain strontium, barium or lanthanum (e.g. those described in U.S. Pat. No. 3,971,754). Some of the fillers may consist of an X-ray-opaque additive, such as for example yttrium trifluoride, strontium hexafluorozirconate or fluorides of the rare earth metals (e.g. according to EP 0 238 025 A1). For better incorporation of the filler into the polymer matrix, it is advantageous to hydrophobize the inorganic fillers. Customary hydrophobization agents include silanes such as 3-glycidyloxypropyl)trimethoxysilane and [2-(3,4-epoxycyclohexyl)-ethyl]trimethoxysilane. The fillers preferably have an average grain size <20 μm, preferably < 5 μm and in particular <2 μm and an upper grain limit of 150 μm, preferably 70 μm and in particular 25 μm. Such fillers can be present in amounts of from about 3 to about 90 weight percent, especially from about 25 to about 80 wt.-% or from about 50 to about 75 wt.-% of the curable composition.

Other suitable fillers are disclosed in U.S. Pat. Nos. 6,387,981 and 6,572,693 as well as in WO 01/30305, WO 01/30306, WO 01/30307 and WO 03/063804. Filler components described in these references include nanosized silica particles, nanosized metal oxide particles, and combinations thereof. Nanofillers are also described in U.S. patent applications entitled, "Dental Compositions Containing Nanozirconia Fillers," Ser. No. 10/847,782; "Dental Compositions Containing Nanofillers and Related Methods," Ser. No. 10/847,781 and "Use of Nanoparticles to Adjust Refractive Index of Dental Compositions", Ser. No. 10/847,803 all three of which were filed on May 17, 2004.

Non-reinforcing fillers also may be used such as quartz, cristobalite, calcium silicate, diatomaceous earth, zirconium silicate, montmorillonite (such as bentonite), zeolite, and molecular sieves (such as sodium aluminium silicate), metal oxide powder (such as aluminium or zinc oxide or their mixed oxides), barium sulphate, calcium carbonate, plaster, glass and plastic powders.

Suitable fillers are also reinforcing fillers such as e.g. pyrogenic or precipitated silicic acid and silica aluminium mixed oxides. The above-mentioned fillers can be hydrophobized, for example by treatment with organosilanes or siloxanes, or by the etherification of hydroxyl groups to alkoxy groups. One type of filler or a mixture of at least two fillers can be used in the invention.

A combination of reinforcing and non-reinforcing fillers is particularly preferred. In this respect, the quantity of reinforcing fillers ranges from about 1 to about 10 wt.-%, in particular from about 2 to about 5 wt.-% of the curable composition.

The difference in the named overall ranges, i.e. about 2 to about 89 wt.-% is accounted for by non-reinforcing fillers.

Pyrogenically-prepared, highly-dispersed, silicic acids which have preferably been hydrophobized by surface treatment are preferred as reinforcing fillers. The surface treatment can be carried out, for example, by treating the filler with dimethyldichlorosilane, hexamethyldisilazane, tetramethylcyclotetrasiloxane or polymethylsiloxane.

Particularly preferred non-reinforcing fillers are quartzes, cristobalites, calcium carbonate and sodium aluminium silicates which can be surface-treated. The surface treatment can generally be carried out with the same methods as described in the case of the reinforcing fillers.

Optional additive components like stabilizers, modifiers, dyes, pigments, thixotropic agents, flow improvers, thinning agents, polymeric thickeners, surfactants, and diluting agent(s) can be added alone or in admixture.

The above described halogenated epoxy functional ether derivatives can be used as monomers in dental compositions that are curable preferably via a cationic ring opening polymerization of epoxy groups.

The dental composition of the present invention can be used, for example, to prepare a dental filling material, crown and bridge material, veneer material, inlay or onlay, pit and fissure sealant, bonding material.

The dental compositions of the invention can be provided as a one-part mixture or as a multiple part mixture. This usually depends on the initiator used. If the initiator is a light cure initiator, the dental composition can be provided as a one-part mixture. If the initiator is a redox cure initiator, the dental composition should be provided as a multiple part mixture.

Therefore, the present invention also relates to a kit of parts, comprising a base part (i) and a catalyst part (ii), wherein the base part (i) comprises one or more halogenated epoxy functional ether derivatives and the catalyst part (ii) comprises initiator. The filler and the optional additive components may be present either in the base part or the catalyst part or in both parts.

The dental compositions of the invention are usually are packaged in a container or cartridge, preferably in a dental compule. Examples of such compules are described in U.S. Pat. Nos. 5,322,440 A1 or 4,391,590 or 5,165,890.

The present invention also relates to a method of producing a curable dental composition comprising the steps
a) providing halogenated epoxy functional ether derivative, initiator, optionally filler and optionally additive components,
b) mixing the components of step a),
wherein the halogenated epoxy functional ether derivative can be obtained via an epoxidation reaction.

Preferably the halogenated epoxy functional ether derivative of the invention can be synthesized via an epoxidation reaction of an olefinic precursor such as the reaction described in Houben-Weyl, Methoden der Organischen Chemie, volume VI/3, p385ff., Georg Thieme Verlag, Stuttgart, 1965, 4. edition.

Preferably, the epoxidation reaction is an oxidation reaction that transforms the C=C double bonds of an olefinic precursor (aa) into a three membered cyclic ethers (cc) by use of an organic peracid $R_2$—$CO_3H$ (bb) as shown below in scheme 1:

scheme 1

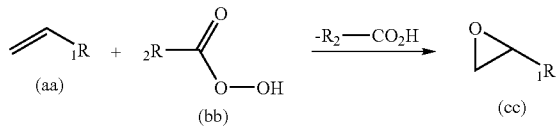

wherein:
$R_1$ represents an aliphatic, cycloaliphatic, aromatic, (cyclo)aliphatic aromatic, or aromatic (cyclo)aliphatic moiety containing at least one aliphatic epoxy group and can be substituted by any atom or moiety that doesn't interfere with the epoxidation reaction e.g. O, Br, Cl, and Si atoms;
$R_2$ represents an aliphatic or aromatic moiety which optionally may be substituted by one or more Br, Cl, F atoms;
wherein $R_1$ is selected such that the three-membered cyclic ether (cc) has no glycidyl ether structure.

For example, the halogenated epoxy functional ether derivative of the invention can be obtained via an epoxidation reaction according to scheme 1 by reacting an aliphatic olefinic precursor (aa) with an organic peracid (bb) as described for similar siloxane based compounds in U.S. Pat. No. 4,788, 268 (preparation examples 1, 2, 4, 5, 6, and 7 in columns 6-17), which disclosure is herein incorporated by reference.

Examples of suitable aliphatic olefinic precursors (aa) include, for example, 1,5-bis(2-allyl-6-chloro-phenoxy)-pentane or 2,2-bis[3,5-dichloro-4-(4-pentenyloxy)-phenyl]-propane which can be synthesized via an etherification of 2-allyl-6-chloro-phenole (which can be synthesized, for example, according to the method described by Tarbell, D., S., Wilson, J., W., *J. Am. Chem. Soc.* 1942, 64(5), 1066-1070)} and 1,5-dibromopentane, 2,2-bis(3,5-dichloro-4-hydroxy-phenyl)-propane or 1-bromo-4-pentene as e.g. described for similar compounds like e.g. allyl-phenyl-ether or but-2-enyl-(2-methoxy-phenyl)-ether within Houben-Weyl, Methoden der Organischen Chemie, volume VI/3, p57 (first preparation example) resp. p. 56 (first preparation example), Georg Thieme Verlag, Stuttgart, 1965, 4. edition or like e.g. allyl-(2-chloro-phenyl)-ether as e.g. described by Tarbell, D., S., Wilson, J., W., *J. Am. Chem. Soc.* 1942, 64(5), 1066-1070.

The following compounds are examples of preferred aliphatic olefinic precursors (aa) used according to scheme 1 for the synthesis of halogenated epoxy functional ether derivative to provide ether derivative compounds according to formula (I):

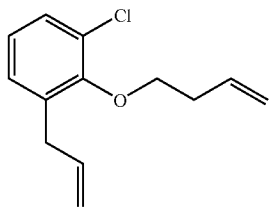

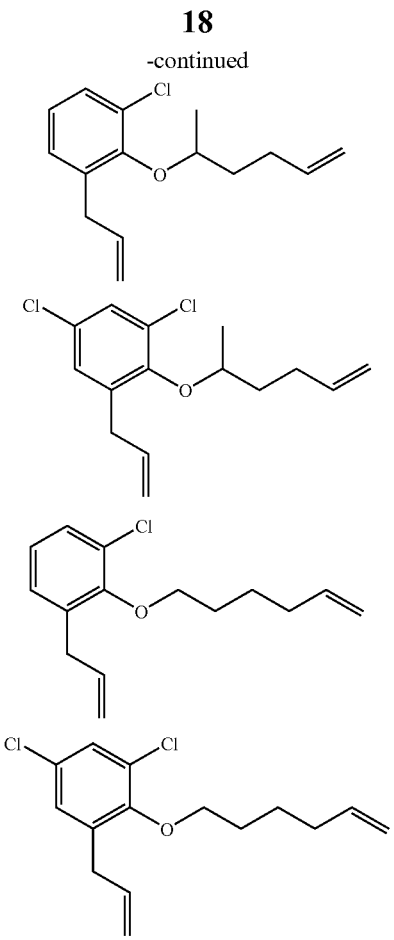

The following compounds are examples of preferred aliphatic olefinic precursors (aa) used according to scheme 1 to prepare halogenated epoxy functional ether derivatives according to formula (II):

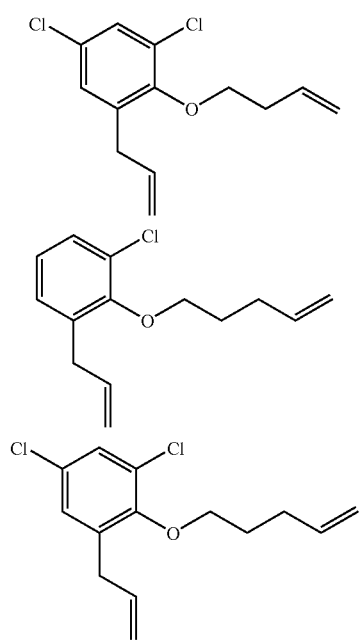

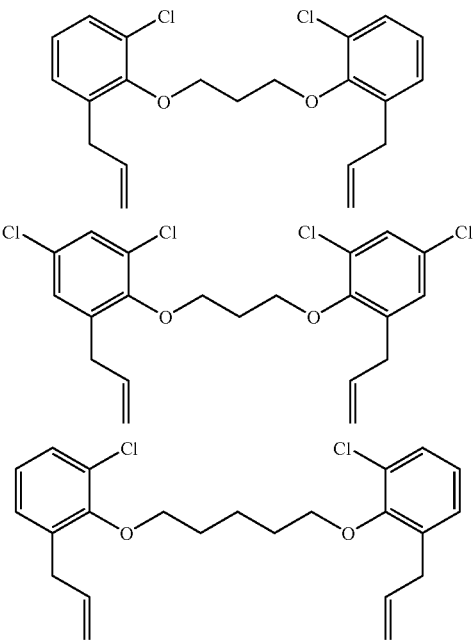

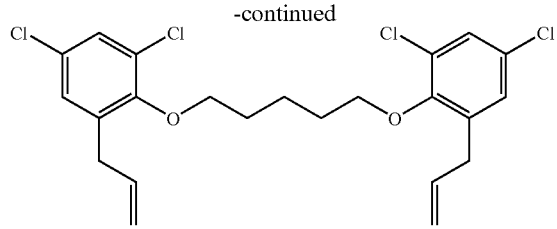
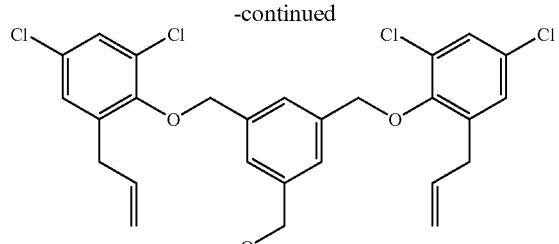
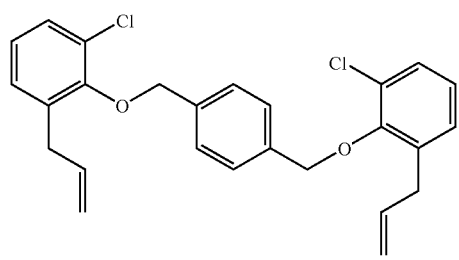
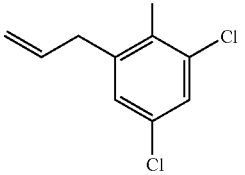
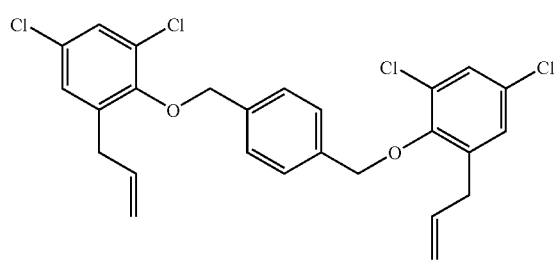
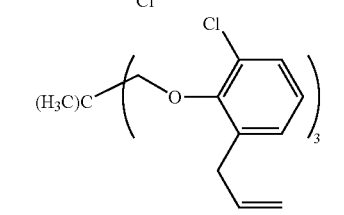
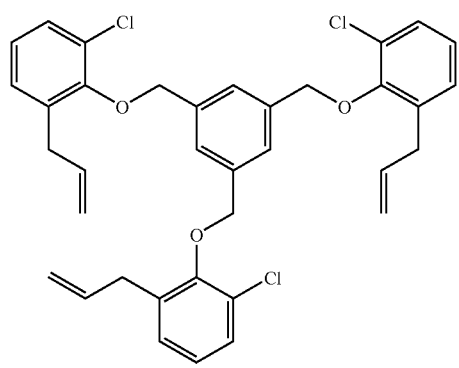
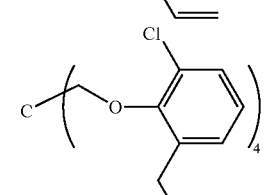
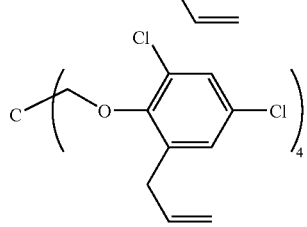
The following compounds are examples of preferred aliphatic olefinic precursors (aa) used according to scheme 1 to prepare halogenated epoxy functional ether derivatives according to formula (III):
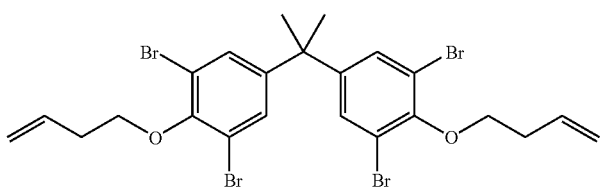

-continued
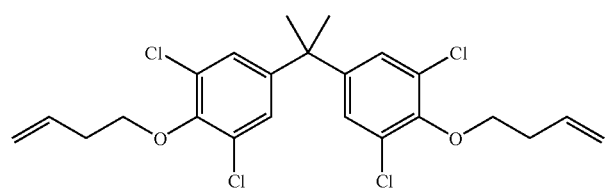
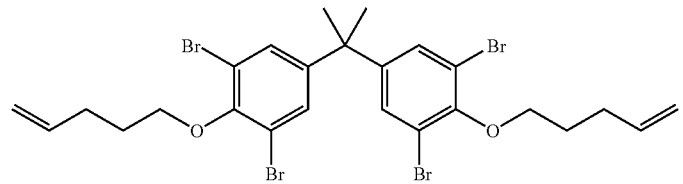
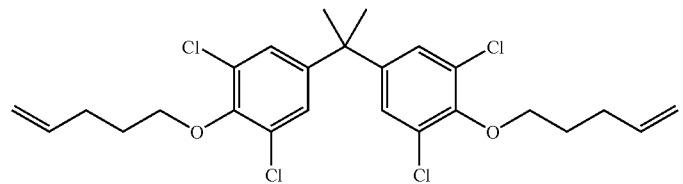
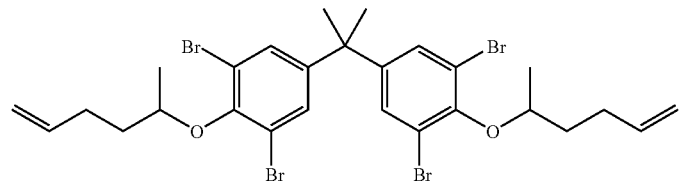
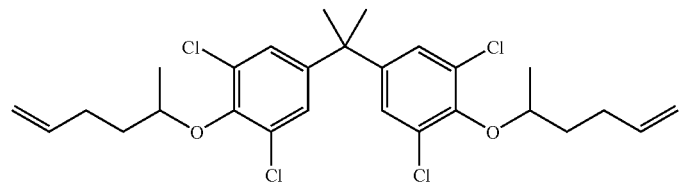
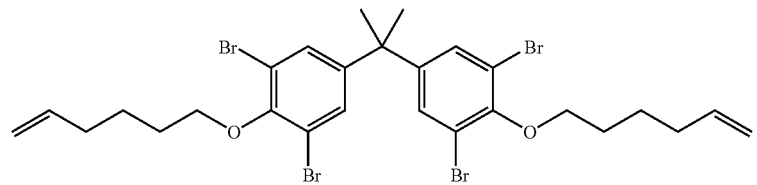
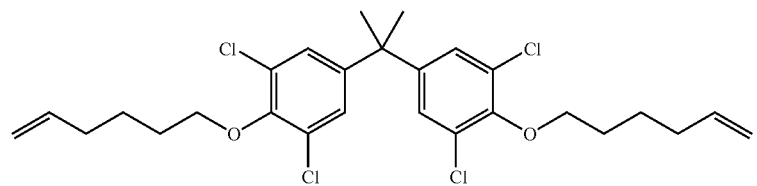
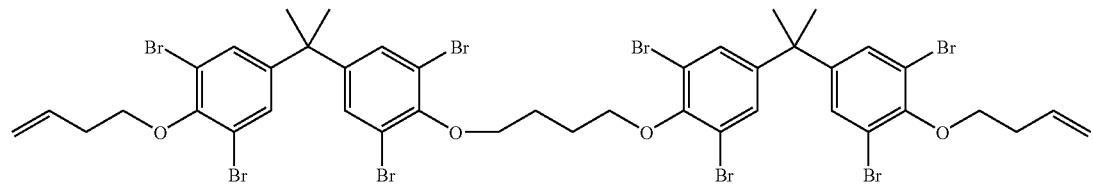
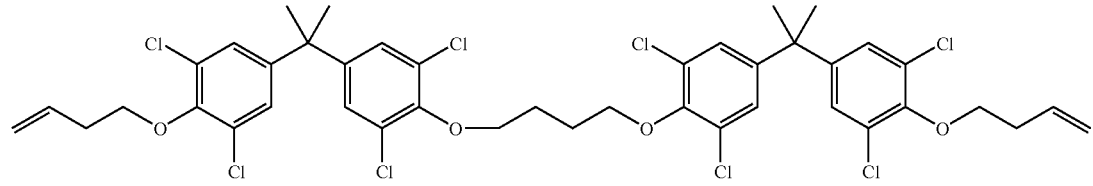

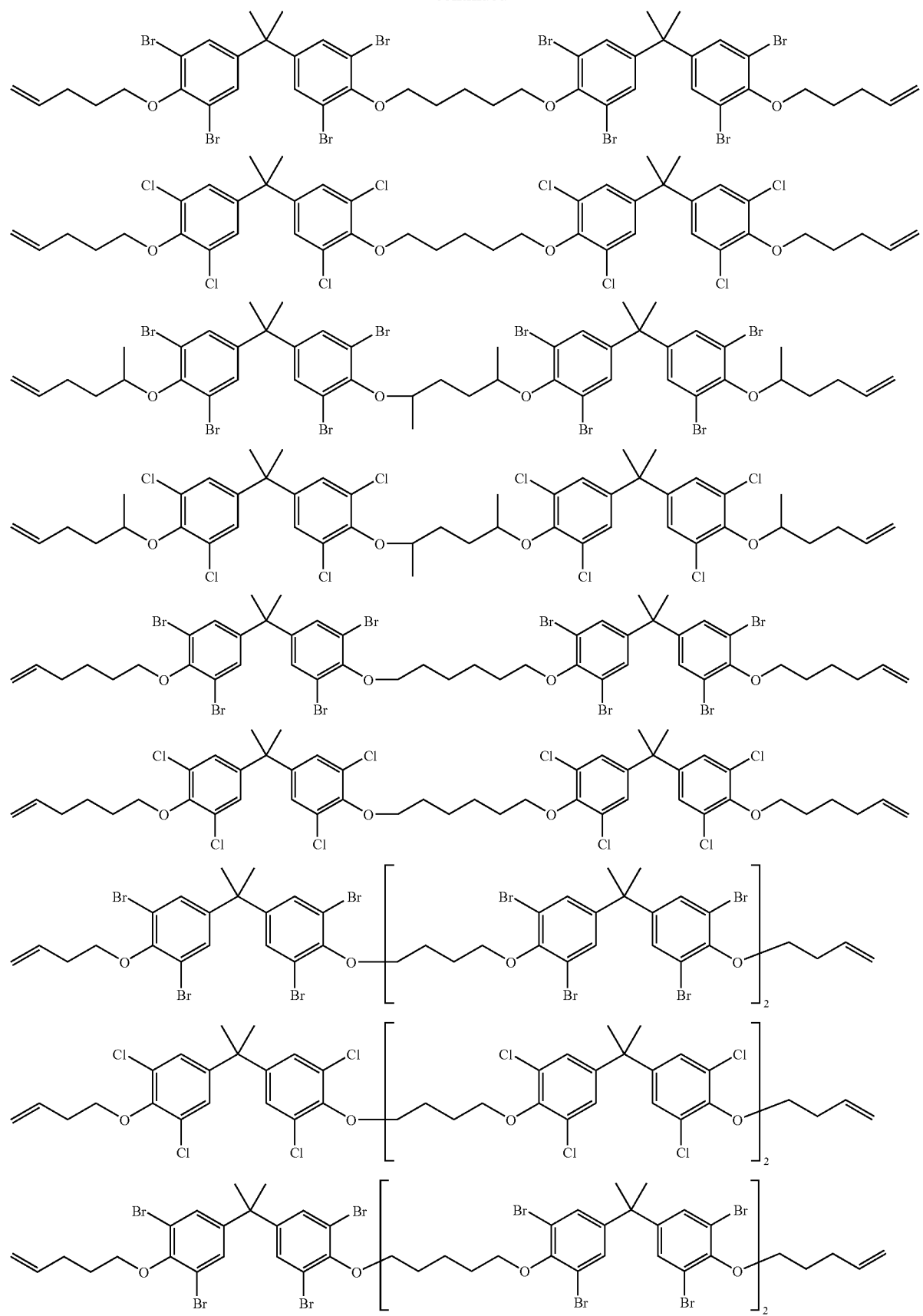

-continued

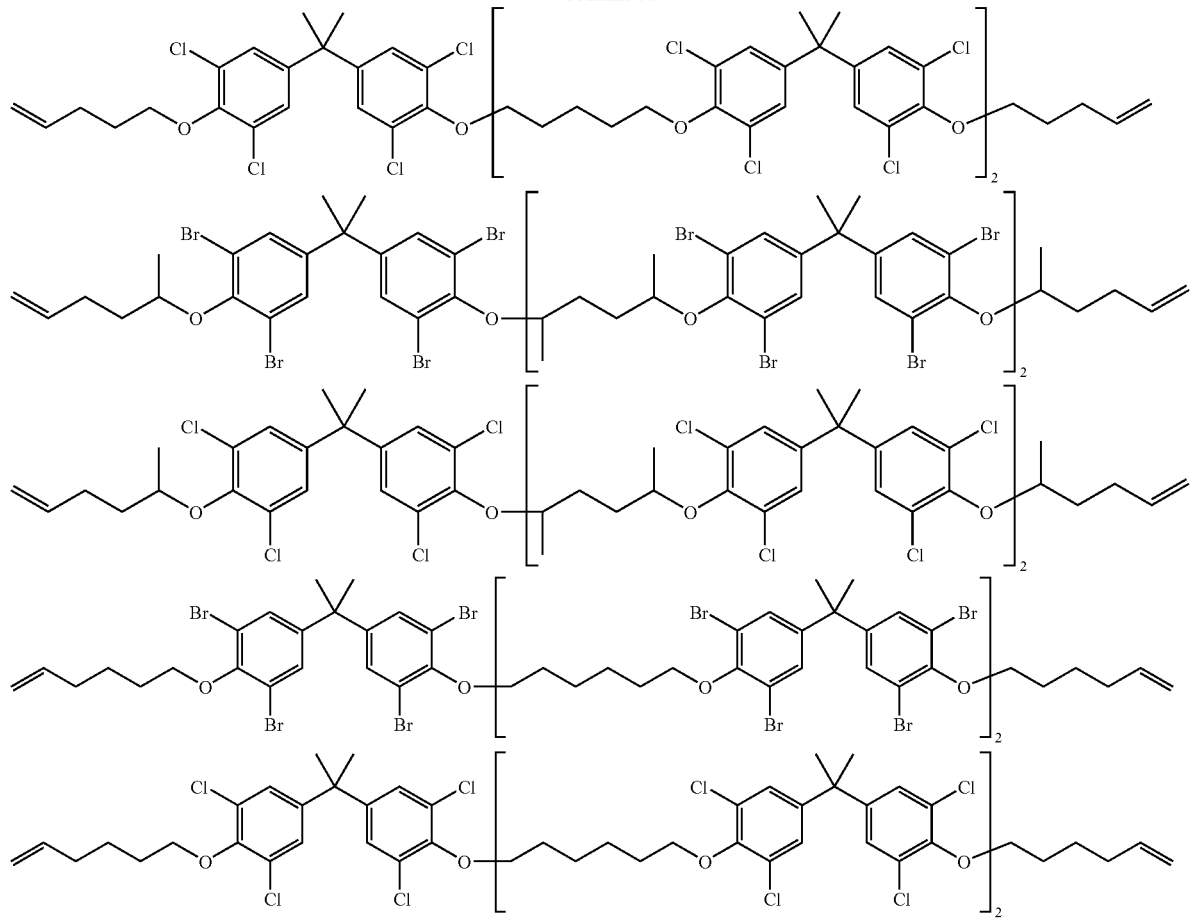

EXAMPLES

The invention is hereinafter described by examples. The examples are for illustrative purpose only and not intended to limit the invention.

If not indicated otherwise, the measurements of the examples were done at standard temperature and pressure ("STP", i.e. 25° C. and 1023 hPa) according to the methods described below.

The refractive index of the halogenated epoxy functional ether derivative was measured with a Kruess AR 4 D device (refractometer according to Abbe's measure principle). The refractive index was measured at 20.0° C. and at a wavelength of 589 nm.

The molecular mass ($M_w$) of the halogenated epoxy functional ether derivative was determined with GPC.

The opacity and the color measurement of the cured dental composition were measured by means of specimens with a defined height of 3.6 (+/−0.1) mm and a diameter of 20 (+/−0.1) mm. These were prepared by filling the material to be checked into suitably high rings, evenly and free of bubbles, and illuminating it in overlapping areas and in the contact every 40 s by means of a lighting device (Trilight®, 3M ESPE) between plane, transparent, silicone oil treated glass slides. Then the opacity was measured after dry storing the specimen additional 24 hours at standard temperature in the dark with the color measuring device "HunterLab Lab-Scan Spectralcolorimeter" of Hunter Lab Associates Laboratory, Inc., USA (Software SpecWare Software Version 1.01) and given by the device in %-values. Then the color was measured after dry storing the specimen additional 24 hours at standard temperature in the dark with the color measuring device "HunterLab LabScan Spectralcolorimeter" of Hunter Lab Associates Laboratory, Inc., USA (12 mm aperture against a black background, Software SpecWare Software Version 1.01) and given by the device as color values on the L* a* b* scale.

The mutagenicity of the halogenated epoxy functional ether derivative according to the AMES mutagenicity testing protocol has been tested according to OECD Guideline 471 and ISO 10993-3 (2003).

The compounds and dental compositions listed in table 1, 2 and 3 were prepared according to the references listed above.

Their refractive index were measured as described above.

The examples nos. 1 to 6 show higher refractive index and higher molecular mass as the reference compounds nos. 1 to 5.

Table 2 shows the color after curing as the L* a* b* Values and the opacities of examples of dental compositions containing the halogenated epoxy functional ether derivatives in comparison to dental compositions containing reference compounds. It can be seen that the examples of dental compositions nos 11 to 17 that contain halogenated epoxy functional ether derivatives of example nos. 1 to 6 have significant lower a* values and b* values. Especially, they demonstrate a low a* value in combination with a low b* value. They further show useful L* values and good opacity.

Table 3 reveals that all of the compounds of examples nos. 1 to 6 are tested non mutagenic according to the AMES mutagenicity testing protocol.

TABLE 1

| Examples of Compounds | Refractive Index | Molecular Mass [g/mol] |
|---|---|---|
| Reference Compound 1: 1,3,5,7-Tetrakis[2-(3,4-epoxycyclohexyl)-ethyl]-1,3,5,7-tetramethyl-cyclotetrasiloxane | 1.496 | 736.2 |
| Reference Compound 2: Bis[2-(3,4-epoxycyclohexyl)-ethyl]-methyl-phenyl-silane | 1.536 | 370.6 |
| Reference Compound 3: Bis[4-(2,3-epoxy-propyloxy)-phenyl]-methane | 1.579 | 312.4 |
| Reference Compound 4: 2,2-Bis[4-(3,4-epoxy-butyloxy)-phenyl]-propane | 1.563 | 368.5 |
| Reference Compound 5: 2,2-Bis[4-(4,5-epoxy-pentyloxy)-phenyl]-propane | 1.551 | 396.5 |
| Example 1: 1,5-Bis[2-(2,3-epoxy-propyl)-6-chloro-phenyl]-pentane | 1.552 | 437.4 |
| Example 2: 1,5-Bis[2-(2,3-epoxy-propyl)-4,6-dichloro-phenyl]-pentane | 1.561 | 506.3 |
| Example 3: 2,2-Bis[3,5-dichloro-4-(4,5-epoxy-pentyloxy)-phenyl]-propane | 1.571 | 534.3 |
| Example 4: 2,2-Bis[3,5-dibromo-4-(3,4-epoxy-butyloxy)-phenyl]-propane | 1.610 | 684.1 |
| Example 5: 2,2-Bis[3,5-dibromo-4-(4,5-epoxy-pentyloxy)-phenyl]-propane | 1.604 | 712.1 |
| Example 6: 4-[2-(2,3-epoxy-propyl)-6-chloro-phenoxy]-1,2-epoxybutane | 1.535 | 254.7 |

TABLE 2

| Amount in %-Weight | Examples of Dental Compositions | | | | | | | | | | |
|---|---|---|---|---|---|---|---|---|---|---|---|
| | 7 | 8 | 9 | 10 | 11 | 12 | 13 | 14 | 15 | 16 | 17 |
| Reference Compound 1 | 13.0 | 13.0 | 13.0 | 13.0 | 13.0 | 13.0 | 13.0 | 13.0 | 13.0 | | |
| Reference Compound 2 | 13.0 | | | | | | 7.8 | 7.8 | 7.8 | | |
| Reference Compound 3 | | 13.0 | | | | | | | | | |
| Reference Compound 4 | | | 13.0 | | | | | | | | |
| Reference Compound 5 | | | | 13.0 | | | | | | | |
| Example 1 | | | | | 13.0 | | | | | 26.0 | |
| Example 2 | | | | | | 13.0 | | | | | |
| Example 3 | | | | | | | 5.2 | | | | |
| Example 4 | | | | | | | | 5.2 | | | |
| Example 5 | | | | | | | | | 5.2 | | |
| Example 6 | | | | | | | | | | | 26.0 |
| Initiator system | I) | I) | I) | I) | I) | I) | I) | I) | I) | I) | I) |
| Filler | II) | II) | II) | II) | II) | II) | II) | II) | II) | II) | II) |
| Color After Curing [L* Value] | 72.7 | 53.8 | 60.9 | 65.4 | 62.9 | 57.8 | 66.7 | 64.9 | 68.1 | 71.2 | 67.6 |
| Color After Curing [a* Value] | −4.7 | 10.9 | −2.5 | −6.3 | −7.4 | −7.7 | −5.0 | −4.5 | −5.5 | −14.9 | −11.0 |
| Color After Curing [b* Value] | 16.6 | 14.2 | 18.1 | 16.3 | 16.0 | 13.6 | 12.7 | 13.9 | 13.8 | 15.3 | 11.0 |
| Opacity [%] | 87.7 | 84.3 | 81.5 | 81.2 | 84.9 | 88.0 | 85.0 | 85.1 | 84.7 | 84.9 | 88.8 |
| Exact Height of Specimen [mm] | (3.7) | (3.6) | (3.6) | (3.7) | (3.6) | (3.6) | (3.6) | (3.6) | (3.7) | (3.7) | (3.7) |

I) Initiator system: 0.8% Tolylcumyliodonium Tetrakis(pentafluorophenyl)borate, 0.1% Anthracene, 0.2% Camphorquinone
II) Filler: 61.0% Silaned Quartz, mean particle size <2 µm; 11.9% $YF_3$

TABLE 3

| Examples of Compounds | Mutagenic [yes/no][1)] |
|---|---|
| Example 1: 1,5-Bis[2-(2,3-epoxy-propyl)-6-chloro-phenyl]-pentane | n[1)] |
| Example 2: 1,5-Bis[2-(2,3-epoxy-propyl)-4,6-dichloro-phenyl]-pentane | n[1)] |
| Example 3: 2,2-Bis[3,5-dichloro-4-(4,5-epoxy-pentyloxy)-phenyl]-propane | n[1)] |
| Example 4: 2,2-Bis[3,5-dibromo-4-(3,4-epoxy-butyloxy)-phenyl]-propane | n[1)] |
| Example 5: 2,2-Bis[3,5-dibromo-4-(4,5-epoxy-pentyloxy)-phenyl]-propane | n[1)] |

[1)]Tested according to the AMES mutagenicity testing protocol, with *Salmonella* Strains TA98 and TA100: tested to be non mutagenic

The invention claimed is:

1. A curable dental composition comprising at least one halogenated epoxy functional ether derivative and an initiator, wherein the halogenated epoxy functional ether derivative is represented by one of the formulas (I) or (II):

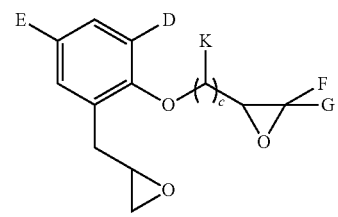

(I)

wherein

D represents Br or Cl,

E represents H, Br or Cl,

F represents H, an alkyl or aryl group having one to 6 carbon atoms, wherein one or more C or H atoms can be replaced by Br, Cl, N or O, G represents H, an alkyl or aryl group having one to 6 carbon atoms, wherein one or more C or H atoms can be replaced by Br, Cl, N or O, each K independently represents H, methyl or ethyl, and c is 3, 4, 5, 6, 7, 8, 9, 10; or

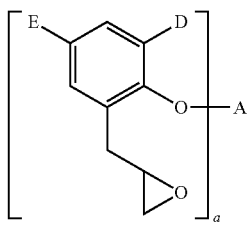

wherein
A represents an alkyl, cycloalkyl, aryl alkyl or aryl cycloalkyl group having one to 12 carbon atoms, wherein one or more C or H atoms can be replaced by Br, Cl, N or O,
each D independently represents Br or Cl,
each E independently represents H, Br or Cl, and
a is 2, 3 or 4.

2. The composition of claim 1 further comprising a filler.

3. The composition of claims 2 further comprising an additive component selected from the group of modifiers, stabilizers, dyes, pigments, thixotropic agents, flow improvers, polymeric thickeners, surfactants, odorous substances, diluting agent(s) and flavorings.

4. The dental composition of claim 3, comprising:
   a) from 1 to 90 wt-% of one or more halogenated epoxy functional ether derivatives,
   b) from 0.01 to 25 wt-% of the initiator,
   c) from 0 to 90 wt-% of the filler, and
   d) from 0 to 25 wt-% of the additive component, with respect to the whole composition.

5. The dental composition of claim 2, wherein the filler comprises reinforcing and/or non-reinforcing fillers.

6. The dental composition of 1, wherein the halogenated epoxy functional ether derivative has a refractive index above 1.530.

7. The dental composition of claim 1, wherein the halogenated epoxy functional ether derivative has a viscosity below 40 Pas.

8. The dental composition of claim 1, wherein the halogenated epoxy functional ether derivative has an average molecular mass from 400 to 10,000 g/mol.

9. The dental composition of claim 1, wherein the opacity of the cured dental composition is above 10%.

10. The dental composition of claim 1, wherein the color formation b* value of the cured dental composition is from about 0 to about 18.

11. The dental composition according to claim 1, wherein the halogenated epoxy functional ether derivative is selected from

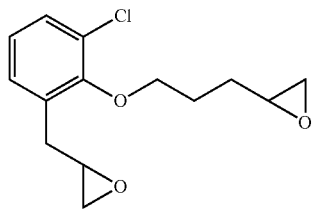

-continued

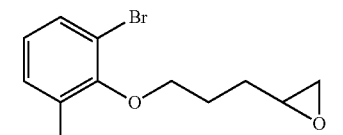

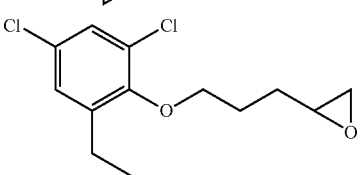

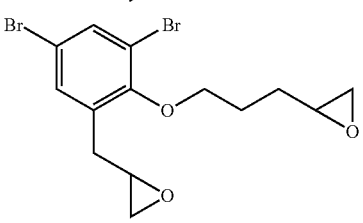

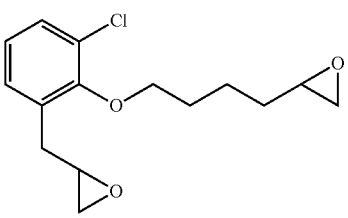

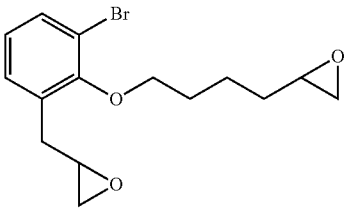

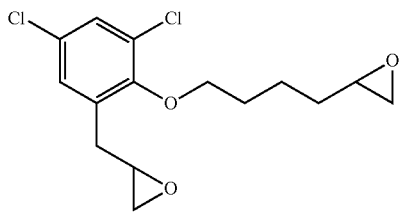

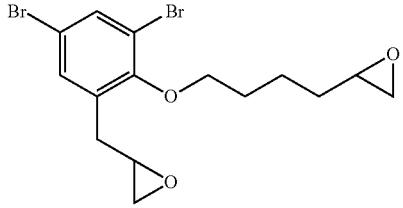

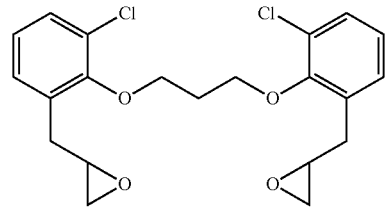

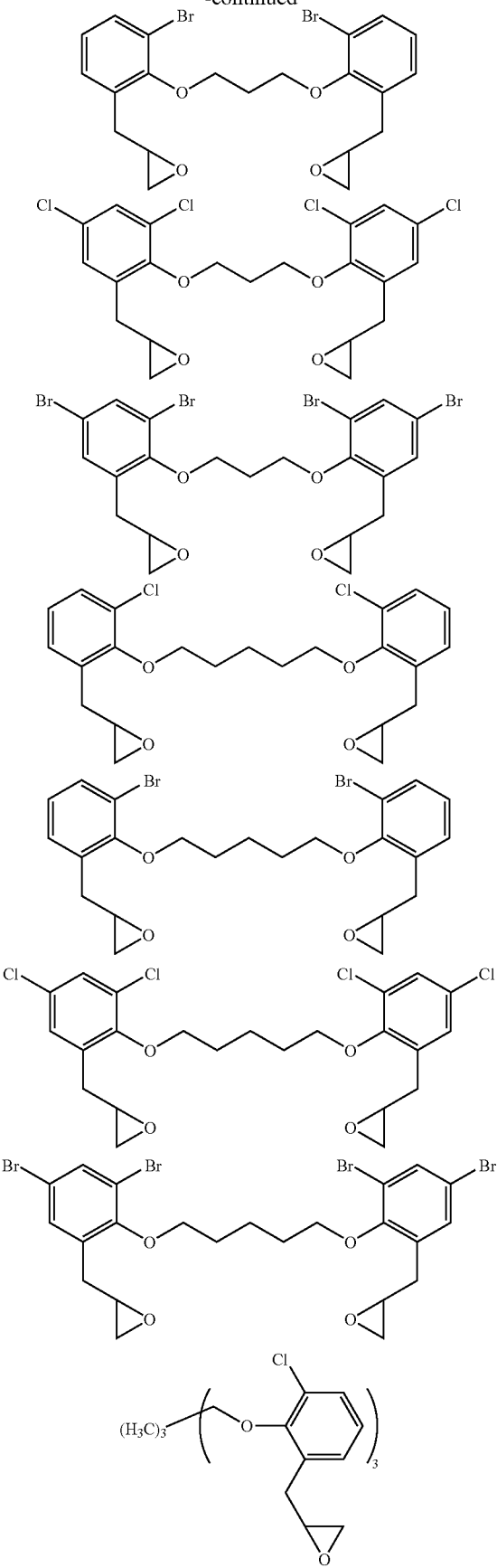

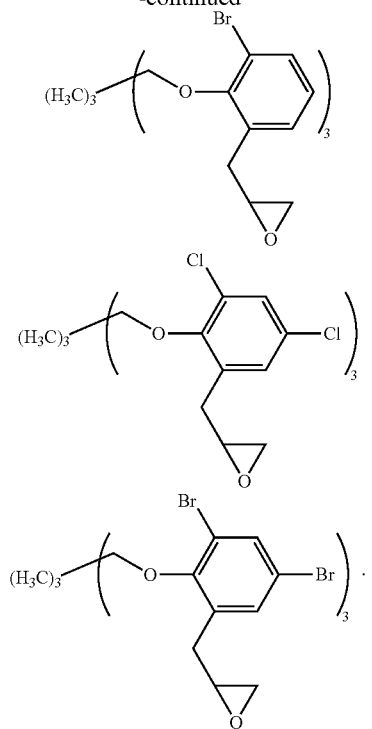

12. The dental composition of claim 1, wherein the initiator comprises a light curing initiator or a redox curing initiator or a combination of both.

13. A cartridge or container containing the dental composition of claim 1.

14. A dental material selected from a dental filling material, a crown or bridge material, a veneer material, an inlay, and an onlay, wherein the material comprises the composition of claim 1.

15. A method for preparing a dental material comprising the steps of:
   a) providing the dental composition of claim 1;
   b) applying the dental composition to a surface; and
   c) curing the dental composition.

16. A kit comprising at least a base part (i) and at least a catalyst part (ii),
   wherein the base part (i) comprises at least one halogenated epoxy functional ether derivative represented by one of the formulas (I) or (II):

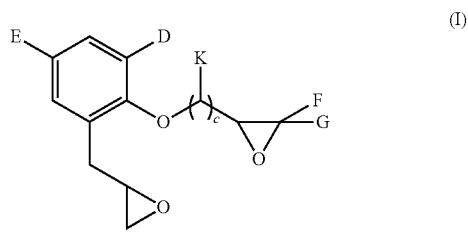

wherein
D represents Br or Cl,
E represents H, Br or Cl,
F represents H, an alkyl or aryl group having one to 6 carbon atoms, wherein one or more C or H atoms can be replaced by Br, Cl, N or O, G represents H, an alkyl or aryl group having one to 6 carbon atoms, wherein one or more C or H atoms can be replaced by Br, Cl, N or O, each K independently represents H, methyl or ethyl, and c is 3, 4, 5, 6, 7, 8, 9, 10; or

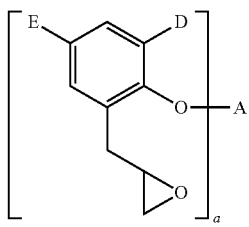

(II)

wherein

A represents an alkyl, cycloalkyl, aryl alkyl or aryl cycloalkyl group having one to 12 carbon atoms, wherein one or more C or H atoms can be replaced by Br, Cl, N or O, each D independently represents Br or Cl, each E independently represents H, Br or Cl, and a is 2, 3 or 4; and the catalyst part (ii) comprises an initiator, and wherein filler and additive components are optionally present either in the base part or the catalyst part or in the base part and the catalyst part.

17. A method of producing a curable dental composition comprising the steps of:

a) providing at least one halogenated epoxy functional ether derivative and an initiator, wherein the halogenated epoxy functional ether derivative is represented by one of the formulas (I) or (II):

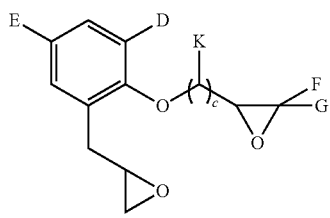

(I)

wherein

D represents Br or Cl,

E represents H, Br or Cl,

F represents H, an alkyl or aryl group having one to 6 carbon atoms, wherein one or more C or H atoms can be replaced by Br, Cl, N or O, G represents H, an alkyl or aryl group having one to 6 carbon atoms, wherein one or more C or H atoms can be replaced by Br, Cl, N or O, each K independently represents H, methyl or ethyl, and c is 3, 4, 5, 6, 7, 8, 9, 10; or

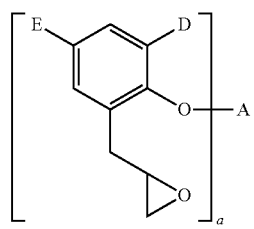

(II)

wherein

A represents an alkyl, cycloalkyl, aryl alkyl or aryl cycloalkyl group having one to 12 carbon atoms, wherein one or more C or H atoms can be replaced by Br, Cl, N or O, each D independently represents Br or Cl, each E independently represents H, Br or Cl, and a is 2, 3 or 4; and b) mixing the components of step a), wherein the halogenated epoxy functional ether derivative is obtainable via an epoxidation reaction.

18. The method according to claim 17, wherein the epoxidation reaction comprises reacting an olefinic precursor compound with an organic peracid.

* * * * *

UNITED STATES PATENT AND TRADEMARK OFFICE
CERTIFICATE OF CORRECTION

PATENT NO. : 7,939,580 B2  
APPLICATION NO. : 11/572051  
DATED : May 10, 2011  
INVENTOR(S) : Adrian Eckert et al.

Page 1 of 1

It is certified that error appears in the above-identified patent and that said Letters Patent is hereby corrected as shown below:

On the Title Page

After "Item [73] Assignee:", after 3M Innovative Properties Company, St. Paul, Minnesota, insert -- and 3M ESPE AG, Seefeld, Germany --.

Signed and Sealed this  
Nineteenth Day of July, 2011

David J. Kappos  
*Director of the United States Patent and Trademark Office*

UNITED STATES PATENT AND TRADEMARK OFFICE
CERTIFICATE OF CORRECTION

PATENT NO. : 7,939,580 B2
APPLICATION NO. : 11/572051
DATED : May 10, 2011
INVENTOR(S) : Adrian Eckert Page 1 of 1

It is certified that error appears in the above-identified patent and that said Letters Patent is hereby corrected as shown below:

Column 1
Following the Title – Add
"Cross Reference to Related Applications

This application is a national stage filing under 35 U.S.C. 371 of PCT/EP2004/007748."

Column 1
Line 27 – Delete "protheses" and insert -- prosthesis --, therefor.

Column 14
Line 55 – Delete "Campherquinone" and insert -- Camphorquinone --, therefor.
Line 56 – Delete "iodoniumium" and insert -- iodonium --, therefor.

Column 15
Line 26 – Delete "Ser. No. 10/847,782" and insert -- Ser. No. 10/847,782 (Attorney Docket No. 59609US002) --, therefor.
Lines 27-28 – Delete "Ser. No. 10/847,781" and insert -- Ser. No. 10/847,781 (Attorney Docket No. 59610US002) --, therefor.
Line 29 – Delete "Ser. No. 10/847,803" and insert -- Ser. No. 10/847,803 (Attorney Docket No. 59611US002) --, therefor.

Column 29
Line 39 – In Claim 6, delete "of 1," and insert -- of claim 1, --, therefor.

Signed and Sealed this
Thirteenth Day of September, 2011

David J. Kappos
*Director of the United States Patent and Trademark Office*